United States Patent [19]

Doncheck et al.

[11] Patent Number: 5,521,090
[45] Date of Patent: May 28, 1996

[54] L-ASCORBIC ACID CONTAINING BIOMASS OF CHLORELLA PYRENOIDOSA

[75] Inventors: James A. Doncheck; Ronald J. Huss; Jeffrey A. Running; Thomas J. Skatrud, all of Manitowoc, Wis.

[73] Assignee: Bio-Technical Resources, Manitowoc, Wis.

[21] Appl. No.: 195,887

[22] Filed: Feb. 10, 1994

Related U.S. Application Data

[63] Continuation-in-part of Ser. No. 853,476, Mar. 18, 1992, abandoned, and Ser. No. 896,724, Jun. 9, 1992, abandoned, and Ser. No. 853,379, Mar. 18, 1992, abandoned, which is a continuation-in-part of Ser. No. 650,886, Feb. 5, 1991, abandoned, which is a continuation of Ser. No. 750,828, Jul. 1, 1985, Pat. No. 5,001,059, said Ser. No. 896,724, is a continuation of Ser. No. 650,886, Feb. 5, 1991, abandoned, which is a continuation of Ser. No. 750,828, Jul. 1, 1985, Pat. No. 5,001,059, said Ser. No. 853,476, is a continuation-in-part of Ser. No. 650,886, Feb. 5, 1991, abandoned, which is a continuation of Ser. No. 750,828, Jul. 1, 1985, Pat. No. 5,001,059.

[51] Int. Cl.$^6$ .............. C12N 1/12; C12N 15/00; C12P 7/58; C12P 7/60
[52] U.S. Cl. .............. 435/257.3; 435/137; 435/138; 435/946; 435/172.1
[58] Field of Search .............. 514/474; 435/257.3, 435/946, 172.1, 137, 138, 136

[56] References Cited

U.S. PATENT DOCUMENTS

5,001,059  3/1991  Skatrud et al. .............. 435/137

OTHER PUBLICATIONS

Loewus, F. A., L–Aseorbic Acid: Metabolism, Biosynthesis, Function The Biochemistry of Plants, vol. 3, pp. 77–99 (1980).

Vaidya et al., Science and Culture (1971) 37:383–384.

Subbulakshmi. et al., Nutirtion Reports International, (1976) 14:581–591.

Shigeoka et al., J. Nutr. Sci. Vitaminol (1979) 29:29–307.

Shigeoka et al., Agric. Biol. Chem. (1979) 43:2053–2058.

Ciferri, Microbiological Reviews (1983) 47:551–578.

Gruen and Loewus, Analytical Biochemisty (1983) 130:191–198.

McNamer et al, Plant Physiol. (1973) 52:561–564.

Reustrom et al., *Plant Sci. Lett*, 28(1982) pp. 299–305.

Aaronson, et al. *Arch Microbiol*, vol. 112, (1977) pp. 57–59.

Vojtisek et al, In "Overproduction of Microbial Metabolites", Butterworths, 1986, pp. 183–198.

*Primary Examiner*—Irene Marx
*Attorney, Agent, or Firm*—Sheridan, Ross & McIntosh

[57] ABSTRACT

Microalgal biomass that comprises cells of *Chlorella pyrenoidosa* which contain greater than 2.0% by dry weight of L-ascorbic acid (Vitamin C), microorganisms and processes that form the biomass, and L-ascorbic acid enhanced animal feed compositions that contain the biomass are disclosed.

5 Claims, No Drawings

L-ASCORBIC ACID CONTAINING BIOMASS OF CHLORELLA PYRENOIDOSA

CROSS-REFERENCE TO RELATED APPLICATIONS

This application is a continuation-in-part of U.S. patent application 07/853,476, filed Mar. 18, 1992, now abandoned, which is a continuation-in-part of U.S. patent application 07/650,886, filed Feb. 5, 1991, now abandoned, which is a continuation of U.S. patent application 06/750,828, filed Jul. 1, 1985, now U.S. Pat. No. 5,001,059; a continuation-in-part of U.S. patent application 07/896,724, filed Jun. 9, 1992, now abandoned, which is a continuation of U.S. patent application 07/650,886, filed Feb. 5, 1991, now abandoned, which is a continuation of U.S. patent application 06/750,828, filed Jul. 1, 1985, now U.S. Pat. No. 5,001,059; and a continuation-in-part of U.S. patent application 07/853,379, filed Mar. 18, 1992, now abandoned, which is a continuation-in-part of U.S. patent application 07/650,886, filed Feb. 5, 1991, now abandoned, which is a continuation of U.S. patent application 06/750,828, filed Jul. 1, 1985, now U.S. Pat. No. 5,001,059, all of which are incorporated herein by reference.

FIELD OF THE INVENTION

This invention relates to microalgal biomass that contains a high intracellular level of L-ascorbic acid (Vitamin C), to microorganisms and to processes that form the biomass, and to L-ascorbic acid enhanced animal feed compositions that comprise the biomass.

BACKGROUND OF THE INVENTION

L-Ascorbic acid, or Vitamin C, is a water-soluble vitamin widely distributed in the plant and animal kingdom. It can be extracted from plant sources, such as paprika, Gladiolus leaves, rose hips, persimmon, and citrus fruit, or synthesized from L-xylose, L-galactose, or D-glucose. F. A. Loewus, L-Ascorbic Acid: Metabolism, Biosynthesis, Function, in *The Biochemistry of Plants,* Vol. 3, Academic Press, New York, 1980, pp. 77–99, reviews the biosynthesis and sources of L-ascorbic acid.

Although most species of animals synthesize L-ascorbic acid, humans and other primates, guinea pigs, fruit eating bats, some birds, and fish such as Coho salmon, rainbow trout channel catfish, and carp cannot. These animals require a dietary source of L-ascorbic acid to prevent scurvy. L-ascorbic acid deficiency in fish also causes scoliosis, lordosis, reduced weight gain, increased susceptibility to bacterial infection, dark skin color, fin erosion, and reduced formation of bone cartilage.

In the wild, fish obtain an adequate amount of L-ascorbic acid from aquatic organisms, such as algae. However, fish grown commercially in high density pens or ponds require supplementary L-ascorbic acid to prevent the problems caused by Vitamin C deficiency. L-Ascorbic acid is formulated into fish food before it is pelletized or extruded, but much of it is lost during production of the feed due to the high levels of moisture, heat (135°–175° C.), and pressure used in extrusion process. Even when ethylcellulose-coated L-ascorbic acid is used, about 50% of the L-ascorbic acid is lost. See R. T. Lovell, *Trans. Am. Fish Soc.,* 107, 321–325 (1978).

Various algae, including Chlorella species, produce L-ascorbic acid. Aaronson, *Arch. Microbiol.* 112, 57–59 (1977) discloses light-grown Chlorella that contain up to 15 µg L-ascorbic acid/mg of dry weight of cells, i.e., 1.5% by weight. Renstrom, *Plant Sci. Letters,* 28, 299–305 (1982/1983) discloses that L-ascorbic acid content in Chlorella is reported to be 6–82 µmol/g dry weight for cells grown in light, i.e., 0.11 to 1.44% by weight. *Chlorella pyrenoidosa* Chick, culture (UTEX) No. 343, dark-grown for 0.5–6 days in a glucose-enriched medium produced about 3 µmol of L-ascorbic acid per g dry weight (0.06 wt %) and four-fold this amount (0.24 wt %) in 12 hours when light was supplied. However, a need exists for biomass containing higher levels of L-ascorbic acid for use as a dietary supplement.

SUMMARY OF THE INVENTION

The invention is a microalgal biomass that comprises cells of *Chlorella pyrenoidosa,* the cells comprising greater than 2.0% by dry weight, preferably greater than 2.5% by dry weight, more preferably greater 4.0% by dry weight, and most preferably greater than 5.0% by dry weight, of L-ascorbic acid. Preferred strains of *Chlorella pyrenoidosa* are *Chlorella pyrenoidosa* ATCC 53170 (UV 101-158) and *Chlorella pyrenoidosa* ATCC 75668 (UV 232-1).

DETAILED DESCRIPTION OF THE INVENTION

Microorganisms

Organisms that produce high levels of L-ascorbic acid have been produced by conventional physical and chemical mutagenizing techniques. Conventional techniques include exposure to radiation, such as ultraviolet irradiation or X-rays, and exposure to a chemical mutating agent, such as, N-methyl-N'-nitro-N-nitrosoquanidine, dimethyl sulfate, ICR 191 (an acridine-based frameshift mutagen), ethyl methane sulfonate, etc. These methods are well know to those skilled in the art.

Strains that produce high levels of L-ascorbic acid can be determined with redox dyes. Using analogs of metabolic intermediates to ascorbic acid or inhibitors of the ascorbic acid synthesis, microorganisms may be selected that are capable of maintaining or increasing L-ascorbic acid production in the presence of chemical interference. These progeny may be separated into individual clones and subjected to the procedures repeated to provide microorganisms that produce even higher levels of L-ascorbic acid.

Preferred microorganisms are green microalgae of the genus Chlorella, in particular the species *Chlorella pyrenoidosa.* High L-ascorbic acid-producing strains of *Chlorella pyrenoidosa* have been derived from such wild strains as *Chlorella pyrenoidosa* UTEX 1663 and *Chlorella pyrenoidosa* UTEX 1230. UTEX is the Culture Collection of Algae, Department of Botany, University of Texas at Austin, Austin, Tex., 78713-7640, USA. Cultures are available to the public for a nominal charge, currently $25.00 each.

Preferred strains of *Chlorella pyrenoidosa* are *Chlorella pyrenoidosa* UV 101- 158, which was deposited with the American Type Culture Collection, 12301 Parklawn Drive Rockville, Md. 20852, USA, on Jun. 27, 1985 and given Accession Number 53 170, and *Chlorella pyrenoidosa* UV232-1, which was deposited with the American Type Culture Collection on Feb. 9, 1994, and given Accession Number 75668.

*Chlorella pyrenoidosa* UV 101-158 was ultimately derived from UTEX 1663 by mutation with ultraviolet light. *Chlorella pyrenoidosa* UV232-1 was derived in turn from NA28-4, NA19-3, UV165-239, UV137-253. UV101-158, UV29-132, UV18-374, UV12-15, UV3-482, and *Chlorella pyrenoidosa* UTEX 1663. The prefixes of the mutant strain names indicate the treatment used to create them: C= camphor; DAP= 2,6-diaminopurine; EMS= ethyl methanesulfonate; NA=nitrous oxide; DAPN= DAP and NA, in succession; SUV= short wavelength ultraviolet light; UV= broad wavelength ultraviolet light.)

Other strains that produce L-ascorbic acid and their parents are as follows. In each case, the mutagenized strain produces more L-ascorbic acid than its parent.

DAPN1010-50 was derived from DAP994-1, which was derived, in turn, from C360-70, C284-130, C284-130, C166-4, SUV551-3, DAP389-23, DAP300-5, UV489- 5, SUV359-2, SUV296-5, SUV97-1, UV213-4, UV212-11, SUV9-1, UV182-2576, NA5-3, UV137-253, UV101-158, UV29-132, UV18-374, UV12-15, UV3-482, and *Chlorella pyrenoidosa* UTEX 1663.

C166-4 was derived from SUV551-3, which was derived, in turn, from DAP389-23, DAP300-5, UV489-5, SUV359-2, SUV296-5, SUV97-1, UV213-4, UV212-11, SUV9-1, UV182-2576, NA5-3, UV137-253, UV101-158, UV29-132, UV18-374, UV12-15, UV3-482, and *Chlorella pyrenoidosa* UTEX 1663.

NA687-1 and C284-130 were derived from C166-4.

NA722-22 was derived from C123-4, which was derived, in turn, from UV609-4, NA528-2 DAP300-6, UV489-5, SUV359-2, SUV296-5, SUV97-1, UV213- 4, UV212-11, SUV9-1, UV182 2576, NA5-3, UV137-253, UV101-158, UV29-132, UV18-374, UV12-15, UV3-482, and *Chlorella pyrenoidosa* UTEX 1663.

Biomass Production

The process may be a conventional heterotrophic fermentation in which the microorganism is grown under unrestricted growth conditions in a growth-promoting medium at an effective temperature, pressure and pH. The medium contains a suitable carbon source, such as glucose, and dissolved molecular oxygen in an amount sufficient for the cells to grow to a high cell density. Growth is continued until the cells contain the desired amount of L-ascorbic acid.

In a preferred process, cells are heterotrophically grown to a high cell density under unrestricted growth conditions. Then, the carbon source is allowed to become substantially depleted so that cell growth substantially ceases. The carbon source is added in restricted amounts so that L-ascorbic acid production continues with substantially no increase in cell density until the L-ascorbic acid concentration reaches the desired level.

A sterile aqueous nutrient culture medium is aseptically inoculated with an actively growing culture of the selected microorganism in amounts sufficient to produce, after a reasonable growth period (during which growth is normally exponential), a relatively high cell density. Initial cell densities are generally about 0.15–0.4 g/L, based on the dry weight of the cells. Small amounts of an antifoaming agent may be added initially or during the process as needed.

The culture medium includes the carbon source, various salts and, generally, trace metals. For reasons of economy, the carbon source is preferably glucose or a source of glucose. Any saccharide or polysaccharide that can be converted in situ to glucose, e.g. molasses, corn syrup, etc, may be used. The total amount of glucose source used can vary broadly depending upon the particular organism and the result desired. Normally, with high L-ascorbic acid producing organisms, the total amount of glucose source used would, if not metabolized, provide a concentration of about 40–100 g/L typically about 60–85 g/L. In general, the total amount of glucose source used (measured in g/L) is about twice the cell density (g/L, dry weight).

Part of the glucose source is normally added initially and the rest during the course of the fermentation. Typically 15–30% of the total glucose is added initially. During the initial glucose source addition and fermentation period the cells are grown to a relatively high density, i.e., 20–50 g/L, typically 30–40 g/L. This permits generation of a high L-ascorbic acid concentration during the carbon-controlled process.

The amount of glucose source in the fermentor should be a non-repressing/non-limiting amount. It should optimally promote, but not inhibit or unduly limit, cell growth. Optimum concentrations of the glucose source may vary from organism to organism, and are readily determined by trial for any particular organism. For *Chlorella pyrenoidosa* strains, glucose source concentrations of 15–30 g/L promote cell growth but do not inhibit growth. Glucose in the supernatant can be determined by the glucose oxidase enzyme test or by high pressure liquid chromatography. When the carbon source concentration drops, it can be replenished as needed. The total concentration should remain below the growth-repressive level, typically about 30 g/L on a glucose-equivalent basis.

Desirably, other additives are present initially along with the glucose source. As known in the art, sources of phosphorus, nitrogen, magnesium, iron and trace metals are required. They may be continually or periodically added to the medium, either separately or in conjunction with the glucose source. A typical nutrient medium is described in U.S. Pat. No. 5,001,059.

The oxygen source is preferably air, but may be molecular oxygen undiluted or diluted with any gas that is not toxic to the microorganism and unreactive with the fermentation components. The oxygen source is conveniently sparged into the fermentation mass The mass is preferably agitated to distribute the gas throughout the medium and facilitate solution of oxygen therein. The availability of the oxygen in the medium, up to the saturation concentration (100% dissolved oxygen) is largely a function of the agitation rate, flow rate, medium composition, temperature and pressure. The availability of dissolved oxygen is easily controlled by controlling the agitation rate and the flow rate.

Depending upon the amount of dissolved oxygen desired at a particular stage of the process, the agitation rate is usually at about 200–1000 rpm and the aeration rate is generally about 0.1–0.6 L of air/minute. During the unrestricted cell growth stage the dissolved oxygen concentration is generally greater than 20% of the saturation value. Preferably, it is 50% or more. The dissolved oxygen concentration is conveniently monitored with an oxygen probe electrode.

The temperature and pressure should be such as to promote cell growth and L-ascorbic acid production without destroying the cells. Normally, the temperature is 20°–40° C., preferably about 35° C. The pressure is generally atmospheric but may be superatmospheric. The greater the pressure the greater the solubility of oxygen in the medium.

The pH can vary widely depending on the ability of the organism to grow, produce and retain intracellular L-ascorbic acid, i.e. resist secreting it into the aqueous medium. In general, with *Chlorella pyrenoidosa* and its various strains, the pH is normally in the range of about 6.5 to 8, more usually about 6.9 to 7.5. Relatively high pHs retard passage of L-ascorbic acid from cell to medium.

To raise pH, gaseous ammonia gas can be added as needed. Ammonia also serves as a source of nutrient nitrogen. To lower pH, a physiologically compatible acid such as phosphoric, acetic, lactic, or tartaric can be added as needed. Since the microorganisms produce acidic byproducts, pH will decrease if base is not added.

During the high oxygen unrestricted growth phase, in which pH is relatively high, intracellular L-ascorbic acid can increase to 1–4 % of the dry weight of the cells. The intracellular L-ascorbic acid content can be increased still further, to at least 2%, preferably greater than 2.5%, more preferably greater 4.0%, and most preferably greater than 5.0% by dry weight of L-ascorbic acid by maintaining the high pH during the low carbon and the low oxygen restricted growth phases.

The biomass may be separated from the medium by conventional separation techniques, such as centrifugation, filtration, etc. Following separation, the biomass may be dried by conventional methods, such as, fluid-bed drying, spray drying, drum drying, etc. Care must be taken to minimize air oxidation or thermal degradation of the L-ascorbic acid content.

INDUSTRIAL APPLICABILITY

Biomass that contains greater than 2.0% by dry weight of L-ascorbic acid is produced. The biomass may be used as animal feed, either directly, or in admixture as an animal feed composition. Isolation and purification of the ascorbic acid is unnecessary. The biomass can be used as a vitamin C supplement for animals, especially in aquaculture. Biomass provides L-ascorbic acid in a more stable form than is provided by other supplements, especially in fish foods, and at the same time provides other nutrients, such as protein to the animal.

The biomass may be fed directly to the animals or mixed with other ingredients to form an animal feed composition. Animal feed compositions for fish typically contain conventional ingredients such as fish meal, soybean meal, distiller's solubles, rice bran and/or hulls, alfalfa meal, peanut meal and/or oil, feather meal, blood meal, and vitamin and mineral supplements. Enriched animal feed compositions typically contain about 60–2,000 g of L-ascorbic acid per ton (907 kg), typically about 320 g/ton.

EXAMPLES 1–4

Medium Preparation. A solution of 0.27 g monobasic potassium phosphate and 0.23 g dibasic sodium phosphate in 600 mL distilled water was heat-sterilized in a 1-L glass equipped with an air inlet and rotating impeller. After the medium had cooled, 5 mL of a 1.92 g/L ferrous sulfate solution (pH 2.5) was added through a 0.2 µ sterile filter.

Glucose Salts Concentrate. The following aqueous nutrient components were separately sterilized, then combined after cooling to a final volume of 109 mL: 80 mL containing 56 g glucose; 10 mL containing 0.70 g trisodium citrate, 0.46 g magnesium sulfate and 0.70 mL 96% sulfuric acid, 10 mL containing 1.53 g monobasic potassium phosphate and 1.53 g dibasic sodium phosphate; and 9.4 mL of the trace metal solution described in Table 1.

TABLE 1

Trace Metal Solution

| COMPONENT | CONCENTRATION[a] (mg/L) |
|---|---|
| calcium chloride, dihydrate | 3102 |
| manganese (II) sulfate, monohydrate | 400 |
| copper (II) sulfate, monohydrate | 0.4 |
| cobalt (II) chloride, pentahydrate | 40 |
| boric acid | 160 |
| zinc (II) sulfate, heptahydrate | 400 |
| sodium molybdate, dihydrate | 19 |
| vanadyl sulfate, dihydrate | 20 |
| nickel (II) nitrate, hexahydrate | 8 |
| sodium selenite | 18 |

[a]Concentration of metal.

Nutrient Medium. Glucose-salts concentrate (20 mL) was then added to the phosphate medium.

Cell Growth and L-Ascorbic Acid Production. The nutrient medium was heated to 35° C. Agitation was begun at 450 rpm. Air was sparged into the medium at 0.1 L/min. The pH was adjusted to 6.9 with anhydrous ammonia added to the airflow. The medium inoculated with an actively growing culture of *Chlorella pyrenoidosa* strain indicated in Table 2 to give an initial cell density of 0.2 g/L.

During the first 10 hr, there was a barely noticeable drop in the dissolved oxygen content of the medium and a slight increase in cell density. After 20 hr, cell growth (g/L cell density) increased and dissolved oxygen decreased to about 70% of the saturation value. Oxygen concentration was measured by an oxygen electrode. After 30 hr, cell density increased to about 5 g/L and oxygen content decreased sharply to less than 20%, reflecting the strong uptake of oxygen by the increasing mass of growing cells. Agitation was increased to nearly 800 rpm and aeration to 0.2 L/min. Dissolved oxygen increased, peaking at about 85%, and then declined to about 25% over the next 10 hr, reflecting the high cell growth rate. Cell density increased to 14 g/L.

Agitation and aeration were held at 775 rpm and 0.2 L/rain respectively over the next 10 hr. Dissolved oxygen dropped to near zero. The rate of cell density increase was at a maximum. Cell density increased to 40 g/L. L-Ascorbic acid increased to 0.8 g/L, substantially all of it intracellular. During the 50 hr growth period, glucose concentration was maintained in excess at 20–30 g/L by addition, as needed, of the glucose-salts concentrate described in U.S. Pat. No. 5,001,059. The pH was maintained at about 6.8–7.0 by addition of anhydrous ammonia to the airflow.

Intracellular L-ascorbic acid was measured by measuring the concentration of ascorbic acid in both the growth medium and in the whole fermentor broth (cells plus growth medium) and calculating the difference. Typically, there was little or no detectable L-ascorbic acid in the broth, indicating the L-ascorbic acid was intracellular. Results are given in Table 2.

TABLE 2

L-ASCORBIC ACID - ENRICHED BIOMASS

| Example | Strain | L-AA (mg/L) | C.D. (g/L) | % L-AA in Biomass |
|---|---|---|---|---|
| 1 | C 166-4 | 834[a] | 34 | 2.4 |
| 2 | NA 687-1 | 999[b] | 38 | 2.6 |
| 3 | NA 722-22 | 852[b] | 36 | 2.4 |

TABLE 2-continued

L-ASCORBIC ACID - ENRICHED BIOMASS

| Example | Strain | L-AA (mg/L) | C.D. (g/L) | % L-AA in Biomass |
|---------|--------|-------------|------------|-------------------|
| 4 | C 284-130 | 792 | 36 | 2.2 |

[a]Average of 2 runs
[b]Average of 3 runs

EXAMPLE 5

A solution of 0.23 g of dibasic sodium phosphate and 0.27 g of monobasic potassium phosphate in 0.6 L of distilled water was sterilized in a 1-L fermentor. To the phosphate solution was aseptically added 11.2 mg of ferrous sulfate heptahydrate in 5 mL distilled water and 20 mL of sterile glucose salts concentrate prepared by individually sterilizing, cooling, and combining: 56 g food-grade glucose monohydrate (anhydrous basis) in 80 mL water; 0.7 g trisodium citrate dihydrate, 0.47 g magnesium sulfate anhydrous and 1 mL sulfuric acid in 10 mL water; 0.65 g monobasic sodium phosphate, 1.3 g monobasic potassium phosphate and 0.6 g dibasic sodium phosphate in 10 mL water; and 9.4 mL of trace metal solution (Table 1).

The temperature was raised to 35° C. and agitation begun at about 200 rpm. Air was passed through the medium at the rate of 0.2 L/min. A culture of *Chlorella pyrenoidosa* ATCC Accession No. 53170 (strain UV 101-158) (50 mL) was added at about 0.3 g cells/L. Fermentation conditions are given in Table 3.

TABLE 3

| Time (hr) | pH | C.D. (g/L) | L-AA[a] (mg/L) | Comments | L-AA in Biomass (% Dry Wt.) |
|-----------|-----|------------|---------------|----------|------------------------------|
| 0 | 6.9 | — | | | |
| 5 | 6.6 | 0.7 | | 400 rpm air 0.4 L/min | Not Determined |
| 16 | 6.9 | 3.8 | | 550 rpm air 0.6 L/min | " |
| 21 | 7.0 | 9.5 | | 700 rpm add 20 mL[b] | " |
| 24 | 6.9 | 14.2 | | 800 rpm add 20 mL[b] | " |
| 36 | | | | glucose depleted | " |
| 40 | 7.1 | 38.6 | 538 | add 4 mL[c] | 1.4 |
| 45 | 7.2 | 38.6 | 654 | | 1.7 |
| 48 | | | | add 4 mL[c] | |
| 51 | 7.6 | 38.1 | 775 | add 2 mL[c] | 2.0 |
| 65 | 7.7 | 37.8 | 966 | | 2.6 |
| 68 | 7.8 | | 1050 | add 4 mLc | |
| 92 | 7.6 | 37.2 | 1292 | | 3.5 |
| 101 | 7.3 | 36.1 | 1459 | | 4.0 |

[a]Intracellular
[b]Glucose salts concentrate
[c]20% Glucose. Addition was repeated as shown.

EXAMPLE 6

The procedure of Example 5 was followed except that: (1) 5.6 mg ferrous sulfate, instead of 11.2 mg, was used in the initial 0.6 L distilled water charge; (2) the nutrient solution consisted of: 28 g glucose in 40 mL distilled water; 0.53 g trisodium citrate dihydrate plus 0.2 g magnesium sulfate in 20 mL; 0.65 g each of monopotassium acid phosphate and disodium acid phosphate in 20 mL; and 4.7 mL of the trace metal solution plus 1 mL sulfuric acid in 15 mL; and (3) the actively growing culture of *Chlorella pyrenoidosa* was strain ATCC 75688.

The temperature was raised to 35° C., agitation begun at 350 rpm, air passed through the medium at 0.2 L/m in, pH adjusted to 6.9 with anhydrous ammonia added to the air flow, and strain UV 232-1 added to the medium. Ammonia was fed throughout the run as nutrient nitrogen source and pH controller. After 6.2 hr the air flow was increased to 0.4 L/min and agitation to 400 rpm. At 11.8 hr the air flow was raised to 0.6 L/rain, where it was held for the remainder of the run. Agitation was increased to 650 rpm. At 12.4 hr, 40 mL of glucose-containing nutrient solution was added to the fermentor, followed by 20 mL at 24.4 hr and 15 mL at 26.3 hr. Agitation was increased to 750 rpm at 22.8 hr. At 34.8 hr it was increased to 800 rpm and maintained there for the rest of the run.

Glucose was depleted at 31.7 hr. Cell density was 19.5 g/L; L-ascorbic acid concentration 322 mg/L. Glucose, 2 mL of 10% solution, was fed to the fermentor at 41.7 hr and every 3 hr thereafter until 94.8 hr. Cell density (C.D.), L-ascorbic acid (L-AA) concentration, pH, and calculated L-ascorbic acid content of 15 the biomass are shown in Table 4.

TABLE 4

| Time hr | pH | C.D. g/L | L-AA mg/L | Comments | Wt. % L-AA |
|---------|-----|----------|-----------|----------|------------|
| 0 | 6.9 | — | | | |
| 6.2 | 6.9 | | | | |
| 11.8 | 6.9 | | | 40 mL glucose at 2.4 hr; 20 mL glucoe at 24.4 hr; 15 mL glucose at 26.3 hr. | |
| 31.7 | 6.9 | | | glucose depleted | |
| 34.8 | 7.0 | 19.5 | 322 | a | 1.7 |
| 46.9 | 7.7 | 18.7 | 429 | | 2.3 |
| 53.6 | 7.8 | | 528 | | |
| 58.6 | 7.8 | 17.9 | 613 | | 3.4 |
| 70.8 | 7.9 | | 694 | | |
| 77.7 | 7.9 | 17.3 | 819 | | 4.7 |
| 82.8 | 7.8 | | 915 | | |
| 94.8 | 7.6 | 17.6 | 945 | | 5.4 |

[a]2 mL 10% glucose added at 41.7 hr and every 3 hr thereafter until 94.8 hr.

The procedure was repeated four more times. In one run Maltrin, a maltodextin (5 g/20 mL distilled water), was added at 47.3 and 71.2 hr as a glucose equivalent carbon source. L-Ascorbic acid averaged 5.2% of the dry weight of the biomass over the 5 runs.

L-Ascorbic acid was measured by ion-exchange on a 7.8×300 mm organic acid analysis column, HPX-87 (Bio-Rad Laboratories, Richmond, Calif.) using the procedure of Grun and Loewus, *Analytical Biochemistry* 130, 191–198 (1983). The conditions were: mobile phase, 0.013 M nitric acid; flow 0.8 mL/min; pressure. 1500 psig; detection, UV 245–254 nm. Resolution of L-ascorbic acid and isoascorbic is possible. All ascorbic acid is intracellular.

To determine cell density (dry weight of cells in g/L) a biomass sample (5 mL) was transferred to one weighing pan and 5 mL of centrifuged supernatant transferred to a second weighing pan. The pans were dried in a convection oven (105° C. for 3 hr). After cooling in a desiccator, the pan contents were weighed. The g of cells/L was determined as: (sample weight—supernate weight) x 200/L.

EXAMPLE 7

The procedure as in Example 1 was followed, except as described below.

Cell Growth and L-Ascorbic Acid Production. The nutrient medium was heated and maintained at 35° C. Agitation was begun at 300 rpm. Air was sparged into the medium at 0.1 L/min and the pH adjusted to 6.9 with anhydrous ammonia added to the airflow. The medium was inoculated with an actively-growing culture of *Chlorella pyrenoidosa* strain DAP388-19 to give an initial cell density of approximately 0.3 g/L dry weight.

In the first stage of the fermentation, the cells were grown to intermediate density. Growth was carried out for 42 hr at a growth rate of 0.12 hr$^{-1}$. Anhydrous ammonia was added to maintain the pH in the range of about 6.5 to 7.0. The pH control was released after active growth. To maintain an excess of dissolved oxygen between 20% and 90% air saturation during the course of the fermentation, the agitation was increased to 800 rpm. Aeration was begun at 0.2 L/min and increased to 0.4 L/min of air. The cell density at the end of the initial phase was 38 g/L.

The intracellular L-ascorbic acid content of the cells (biomass) at the end of the run was 2.7%, based on the dry weight of the cells.

Cell Drying. Cells were harvested by centrifugation. The cell paste was loaded into a syringe and extruded onto the supporting screen of a fluid-bed dryer. Cells were dried by blowing air up through the screen at the maximum blower speed for 65 min, at an outlet temperature of 70° C. Moisture content was determined by the dry weight procedure above. L-ascorbic acid content of the cells was determined by the method of Grun and Loewus. Aliquots of dried cells were placed in screw-capped vials and stored at room temperature (25° C.). Portions of these stored cells were removed and assayed for both moisture and L-ascorbic acid. The results are given in Tables 5 and 6.

TABLE 5

| | Drying | |
|---|---|---|
| Time, (min) | Percent moisture | mg L-AA per gram of cells |
| 0 | 79.1 | 24.2 |
| 18 | 11.1 | 22.2 |
| 31 | 6.8 | 24.3 |
| 42 | 5.2 | 22.4 |
| 53 | 4.9 | 22.6 |
| 65 | 4.2 | 23.2 |

TABLE 6

| | Storage (25° C.) | |
|---|---|---|
| Time (days) | Moisture (%) | mg L-AA per gram of cells |
| 0 | 5.2 | 21.8 |
| 11 | 4.0 | 23.5 |
| 25 | 5.8 | 23.3 |
| 33 | 5.2 | 21.2 |
| 74 | 4.3 | 17.2 |

Less than 4% of the L-ascorbic acid was lost during drying. The half-life of L-ascorbic acid in the dried cells was about 150 days. The half-life of L-ascorbic acid in pelleted fish feed is about 90 days. (See *Nutrient Requirements of Warmwater Fishes,* National Academy of Sciences, Washington, D.C., 1977, p. 28.)

What is claimed is:

1. A culture of *Chlorella pyrenoidosa* ATCC 53170.

2. A culture of *Chlorella pyrenoidosa* ATCC 75668.

3. A composition comprising cells of *Chlorella pyrenoidosa* having all of the identifying characteristics of cells selected from the group consisting of *Chlorella pyrenoidosa* ATCC 53170 and *Chlorella pyrenoidosa* ATCC 75668, wherein said cells of *Chlorella pyrenoidosa* have an intracellular L-ascorbic acid content of at least about 2% by dry weight of said cells.

4. The composition as claimed in claim 3, wherein said cells of *Chlorella pyrenoidosa* have an intracellular L-ascorbic acid content of at least about 4.0% by dry weight.

5. The composition as claimed in claim 3, wherein said cells of *Chlorella pyrenoidosa* have all the identifying characteristics of *Chlorella pyrenoidosa* ATCC 75668 and wherein said cells of *Chlorella pyrenoidosa* have an intracellular L-ascorbic acid content of at least about 5.0% by dry weight.

* * * * *